United States Patent
Haffner et al.

(10) Patent No.: US 7,196,201 B2
(45) Date of Patent: Mar. 27, 2007

(54) PYRROLIDINES AS DIPEPTIDYL PEPTIDASE INHIBITORS

(75) Inventors: Curt Dale Haffner, Durham, NC (US); Darryl Lynn McDougald, Durham, NC (US); Amarjit Sab Randhawa, Durham, NC (US); Steven Michael Reister, Durham, NC (US); David N Deaton, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 409 days.

(21) Appl. No.: 10/481,288

(22) PCT Filed: Jun. 26, 2002

(86) PCT No.: PCT/US02/20466

§ 371 (c)(1),
(2), (4) Date: Dec. 19, 2003

(87) PCT Pub. No.: WO03/002530

PCT Pub. Date: Jan. 9, 2003

(65) Prior Publication Data

US 2004/0167341 A1  Aug. 26, 2004

Related U.S. Application Data

(60) Provisional application No. 60/387,011, filed on Jun. 6, 2002, provisional application No. 60/301,333, filed on Jun. 27, 2001.

(51) Int. Cl.
*C07D 207/16* (2006.01)
*C07D 277/04* (2006.01)
(52) U.S. Cl. ....................... 548/200; 548/540
(58) Field of Classification Search ............... 548/200, 548/540; 514/365, 423
See application file for complete search history.

(56) References Cited

U.S. PATENT DOCUMENTS

| | | | | |
|---|---|---|---|---|
| 5,939,560 A * | 8/1999 | Jenkins et al. | ............... | 548/535 |
| 6,011,155 A | 1/2000 | Villhauer | | |
| 6,090,786 A | 7/2000 | Augustyns et al. | | |
| 6,124,305 A | 9/2000 | Villhauer | | |
| 6,166,063 A | 12/2000 | Villhauer | | |
| 6,946,480 B2 * | 9/2005 | Demuth et al. | ............. | 514/365 |
| 7,026,316 B2 * | 4/2006 | Ashton et al. | ............... | 514/242 |

| | | | |
|---|---|---|---|
| 2002/0019411 A1 | 2/2002 | Robl et al. | |
| 2006/0111336 A1 * | 5/2006 | Duffy et al. ........... | 514/210.17 |

FOREIGN PATENT DOCUMENTS

| | | |
|---|---|---|
| EP | 1 245 568 | 3/2002 |
| EP | 1 333 025 | 8/2003 |
| WO | 98/19998 | 5/1998 |
| WO | 99/38501 | 8/1999 |
| WO | 99/61431 | 12/1999 |
| WO | 00/34241 | 6/2000 |
| WO | 00/56296 | 9/2000 |
| WO | 01/14318 | 3/2001 |
| WO | 01/34594 | 5/2001 |
| WO | 01/40180 | 6/2001 |
| WO | 01/52825 | 7/2001 |
| WO | 01/62266 | 8/2001 |
| WO | 01/81304 | 11/2001 |
| WO | 01/81337 | 11/2001 |
| WO | 01/96295 | 12/2001 |
| WO | 02/02560 | 1/2002 |
| WO | 02/30890 | 4/2002 |
| WO | 02/30891 | 4/2002 |
| WO | 02/38541 | 5/2002 |
| WO | 02/076450 | 10/2002 |
| WO | 02/83128 | 10/2002 |
| WO | 03/000180 | 1/2003 |
| WO | 03/000250 | 1/2003 |
| WO | 03/35067 | 5/2003 |

OTHER PUBLICATIONS

Li et al., Archives of Biochemistry and Biophysics, 323(1), 148-154, 1995.*

* cited by examiner

*Primary Examiner*—Fiona T. Powers
(74) *Attorney, Agent, or Firm*—Amy H. Fix

(57) ABSTRACT

The present invention relates to novel compounds, their use for inhibiting serine proteases, such as dipeptidyl peptidases, such as dipeptidyl peptidase IV (DPP-IV) and to methods for their production and their therapeutic utility (I)

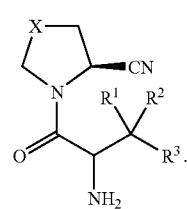

1 Claim, No Drawings

PYRROLIDINES AS DIPEPTIDYL PEPTIDASE INHIBITORS

This This application is filed pursuant to 35 U.S.C. § 371 as a United States National Phase Application of International Application No. PCT/US02/20466 filed Jun. 26, 2002, which claims priority from U.S. 60/301,333 filed Jun. 27, 2001 and U.S. Ser. No. 60/387,011 filed Jun. 6, 2002.

FIELD OF INVENTION

The present invention relates to compounds inhibiting dipeptidyl peptidases, such as II (DPP-II) and IV (DPP-IV), to methods for their production, and to their therapeutic utility.

BACKGROUND OF THE INVENTION

Dipeptidyl peptidase IV (DPP-IV) is a post-proline/alanine cleaving serine protease found in various tissues of the body including kidney, liver, and intestine. DPP-IV is thought to regulate the activity of multiple physiogically important peptides, including, but not limited to, GLP1, GIP, GLP2, GRP, vasoactive intestinal peptide, peptide histidine methionine, PYY, substance P, beta-casomorphine, NPY, PACAP38, prolactin, chorionic gonadotropin, aprotinin, corticotropin-like intermediate lobe peptide, pituitary adenylyl cyclase-activating peptide, (Tyr)melanostatin, LD78beta (3–70), RANTES, eotaxin procolipase, enterostatin, vasostatin 1, endomorphin, morphiceptin, stromal cell derived factor, macrophage-derived chemokine, granulocyte chemotactic protein-2, and GHRH/GRF. As examples of the therapeutic value of DPP-IV, DPP-IV is believed to be involved in a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure; tumors, and stress-induced abortions, for example cytokine-mediated murine abortions. For example, DPP-IV, also known as CD26, mediates T-cell activation and HIV infection (Ohtsuki et al., 2000). T-cells expressing DPP-IV/CD26 are preferentially infected and depleted in HIV-infected individuals (Ohtsuki et al., 2000). DPP-IV inhibitors have demonstrated anti-inflammatory effects in animal models of arthritis (Tanaka et al, 1997). Additionally, DPP-IV inhibition has been shown to prolong cardiac transplant survival (Korom et al., 1997). In vitro studies suggest that DPP-IV/CD26 expression correlate with tumor progression of malignant melanomas of the skin (Van den Oord, 1998). Furthermore, DPP-IV is thought to regulate metabolism by cleaving the penultimate proline/alanine at the amino-terminus of polypeptides (Mentlein, 1999), such as glucagon-like peptides (GLP) and neuropeptide Y (NPY).

More specifically, GLPs help metabolize glucose and, thus, regulation of GLPs likely should be beneficial in the treatment of metabolic disorders such as diabetes. Diabetes, for example type 2 (also called noninsulin-dependent diabetes mellitus (NIDDM) or maturity-onset) diabetes, results in elevated blood sugar levels due to absolute or relative insufficiencies of insulin. Type 2 diabetes is the more common form of diabetes, accounting for 90% of cases, or about 16 million Americans. Most type 2 diabetics produce variable, sometimes normal, amounts of insulin, but they have abnormalities in liver and muscle cells that resist its actions. Insulin attaches to the receptors of cells, but glucose does not get inside, a condition known as insulin resistance. Many type 2 diabetics seem to be incapable of secreting enough insulin to overcome insulin resistance. GLP-1 enhances insulin secretion. Thus, regulation of GLP-1 correlates to a regulation of insulin secretion. Moreover, GLP-1 decreases hepatic glucose production, gastric emptying, and food intake (Deacon et al., 1995). Further, GLP-2 maintains the integrity of the intestinal mucosal epithelium via effects on gastric motility, nutrient absorption, crypt cell proliferation and apoptosis, and intestinal permeability (Drucker, 2001).

DPP-IV inhibitors preserve GLP-1 function for a longer time (Balka, 1999). Thus, DPP-IV inhibitors may promote satiety, weight loss, and the antidiabetic effects of GLP-1 (Deacon et al., 1995; Hoist and Deacon, 1998). For example, inhibition of DPP-IV with the known compound NVP-DPP728 increases plasma GLP-1 (2–36 amide) concentrations and improves oral glucose tolerance in obese Zucker rats. See, Diabetologia 42: 1324–1331. Both subcutaneously and intravenously administered GLP-1 is rapidly degraded from the $NH_2$-terminus in type II diabetic patients and in healthy subjects. See, Diabetes 44:1126, 1995.

Moreover, DPP-IV inhibitors preserve GLP-2 for longer periods of time and, thus, may be useful for treating intestinal insufficiencies and mucous membrane disorders (Hartmann B et al., 2000).

While DPP-IV is the predominate protease regulating GLP turnover, similar substrate or inhibitor specificity may be observed for related proteases. Related serine proteases include, but are not limited to, dipeptidyl peptidase-II (DPP-II), dipeptidyl peptidase IV beta, dipeptidyl peptidase 8, dipeptidyl peptidase 9, aminopeptidase P, fibroblast activating protein alpha (seprase), prolyl tripeptidyl peptidase, prolyl oligopeptidase (endoproteinase Pro-C), attractin (soluble dipeptidyl-aminopeptidase), acylaminoacyl-peptidase (N-acylpeptide hydrolase; fMet aminopeptidase) and lysosomal Pro-X carboxypeptidase (angiotensinase C, prolyl carboxypeptidase). Proline-cleaving metallopeptidases that may share similar substrate or inhibitor specificity to DPP-IV include membrane Pro-X carboxypeptidase (carboxypeptidase P), angiotensin-converting enzyme (Peptidyl-dipeptidase A multipeptidase], collagenase 1 (interstitial collagenase; matrix metalloproteinase 1; MMP-1; Mcol-A), ADAM 10 (alpha-secretase, myelin-associated disintegrin metalloproteinase), neprilysin (atriopeptidase; CALLA; CD10; endopeptidase 24.11; enkephalinase), Macrophage elastase (metalloelastase; matrix metalloproteinase 12; MMP-12], Matrilysin (matrix metalloproteinase 7; MMP-7), and neurolysin (endopeptidase 24.16; microsomal endopeptidase; mitochondrial oligopeptidase). See http://merops.iapc.bbsrc.ac.uk/.

Furthermore, beyond mammalian serine peptidases and proline-cleaving metallopeptidases, other non-mammalian proteases may share similar substrate or inhibitor specificity to DPP-IV. Non-limiting examples of such non-mammalian serine proteases include prolyl aminopeptidase (prolyl iminopeptidase), IgA1-specific serine type prolyl endopeptidase (IgA protease, *Neisseria, Haemophilus*), dipeptidyl aminopeptidase A (STE13) (*Saccharomyces cerevisiae*), dipeptidyl aminopeptidase B (fungus), prolyl oligopeptidase homologue (*Pyrococcus* sp.), oligopeptidase B (*Escherichia coli* alkaline proteinase II; protease II), dipeptidyl aminopeptidase B1 (*Pseudomonas* sp.), dipeptidyl-peptidase IV (bacteria), dipeptidyl aminopeptidase (*Aureobacterium*), dipeptidyl-peptidase IV (insect), dipeptidyl-peptidase V, allergen Tri t 4 (*Trichophyton tonsurans*), secreted alanyl DPP (*Aspergillus oryzae*), peptidase II-mes (*Prosopis velutina*), and bamboo serine proteinase (*Pleioblastus hindsii*). Non-limiting examples of such non-mammalian proline-cleaving metallopeptidases include penicillolysin (fungal acid metalloendopeptidase), proline-specific peptidyl-dipeptidase (*Streptomyces*), coccolysin (gelatinase, *Enterococcus faecalis*), aminopeptidase Ey, (hen egg yolk) (apdE g.p.; *Gallus gallus domesticus*), gametolysin (*Chlamydomonas* cell wall degrading protease), and snake venom proline-cleaving metalloproteases as well. See http://merops.iapc.bbsrc.ac.uk/ for further reference.

Dipeptidyl peptidase II (DPP II) is a serine protease localized to lysosomes in cells and believed to be involved in lysosomal degradation and protein turnover. The order of expression of DPP-II is kidney>>testis>or=heart>brain>or=lung>spleen>skeletal muscle>or=liver (Araki H et al., J Biochem (Tokyo) 2001, 129:279–88). This expression suggests possible utility in kidney or lysosomal-related disorders. Substrate specificity studies indicated that purified DPP-II hydrolyzes specifically alanine or proline residues at acidic pH (4.5–5.5). DPP-II has significant sequence homology and substrate specificity to quiescent cell proline dipeptidase and prolyl carboxypeptidase, suggesting possible overlapping functions between these proteases (Araki H et al., J Biochem (Tokyo) 2001, 129:279–88).

The present invention includes novel DPP-II and/or DPP-IV inhibitors, as well as methods of their therapeutic use and methods of their production. While not being limited thereby, the compounds of the present invention are believed useful for the treatment of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, psychosomatic, depressive, and neuropsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions, for example cytokine-mediated murine abortions.

SUMMARY OF THE INVENTION

The present invention includes compounds of formula (I):

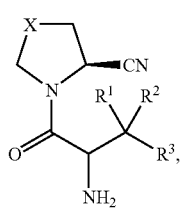

(I)

including salts, solvates, and pharmaceutically functional derivatives thereof, wherein X is —S(O)$_b$— or —CH$_2$—; b is 0–2; $R^1$ and $R^2$ each are either H; alkyl; optionally substituted aryl or heteroaryl; or combine to form a 3 to 14 membered ring sytem, optionally containing one or more heteroatoms, and optionally containing one or more degrees of unsaturation; when $R^1$ and $R^2$ are optionally substituted aryl or heteroaryl, then $R^3$ is H or alkyl; when $R^1$ and $R^2$ are otherwise, then $R^3$ is

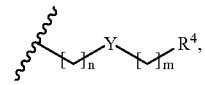

where n is 0–5; m is 0 to 12; Y is S(O)$_p$, O, alkylene, alkenylene, alkynylene, or a bond; p is 0–2; $R^4$ is $R^5$ when Y is S, O, alkylene, alkenylene, alkynylene, or a bond, where $R^5$ is alkyl, alkenyl, alkynyl, aryl, cycloalkyl, heteroaryl, or heterocyclyl; and $R^4$ is $R^6$ when Y is S(O) or S(O)$_2$, where $R^6$ is alkyl, aryl, cycloalkyl, heteroaryl, amino, alkylamino, arylamino, heteroarylamino, or cycloalkylamino.

In one embodiment, $R^1$ and $R^2$ are each alkyl and $R^3$ is

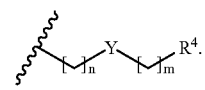

Preferably, each alkyl is $C_1$–$C_6$ alkyl. More preferably, each of alkyl is methyl.

In a particular compound included within the present invention X is —S(O)$_b$—, b is 0, n is 0, m is 1, Y is —S(O)$_p$—, p is 0, $R^4$ is $R^5$, and $R^5$ is optionally substituted aryl. Preferably, $R^5$ is phenyl substituted with alkoxy.

In a particular compound included within the present invention X is —CH$_2$—, n is 0, m is 1, Y is —S(O)$_p$—, p is 0, $R^4$ is $R^5$, and $R^5$ is optionally substituted aryl. Preferably, $R^5$ is phenyl substituted with alkoxy.

In a particular compound included within the present invention X is —CH$_2$—, n is 0, m is 1, Y is S(O)$_p$, p is 2, $R^4$ is $R^6$, and $R^6$ is optionally substituted aryl. Preferably, $R^6$ is phenyl substituted with alkoxy.

In a particular compound included within the present invention X is S(O)$_b$, b is 2, n is 0, m is 1, Y is S(O)$_p$, p is 2, $R^4$ is $R^6$, and $R^6$ is optionally substituted aryl. Preferably, $R^6$ is phenyl substituted with alkoxy.

In certain embodiments, preferably the depicted NH$_2$ group is cis to the depicted nitrile warhead. In other embodiments, preferably the depicted NH$_2$ group is trans to the depicted nitrile warhead.

Particularly preferred compounds of the present invention include:

(4R)-3-{(2R)-2-Amino-3-[(4-methoxybenzyl)thio]-3-methylbutanoyl}-1,3-thiazolidine-4-carbonitrile hydrochloride;

(2S)-1-{(2R)-2-Amino-3-[(4-methoxybenzyl)thio]-3-methylbutanoyl}pyrrolidine-2-carbonitrile hydrochloride;

(2S)-1-{(2R)-2-Amino-3-[(4-methoxybenzyl)sulfonyl]-3-methylbutanoyl}pyrrolidine-2-carbonitrile hydrochloride;

(4R)-3-{(2R)-2-Amino-3-[(4-methoxybenzyl)sulfonyl]-3-methylbutanoyl}-1,3-thiazolidine-4-carbonitrile 1,1-dioxide hydrochloride; and (2S)-1-[(2S)-2-Amino-3,3-bis(4-fluorophenyl)propanoyl] pyrrolidine-2-carbonitrile hydrochloride.

The present invention also includes pharmaceutical formulation comprising a compound of the present invention as herein described. More preferably, the pharmaceutical formulation further includes a pharmaceutically acceptable carrier.

The present invention also includes a method of inhibiting a post proline/analine cleaving protease comprising administering a compound of the present invention as herein described. Preferably, the post proline/analine cleaving protease is a serine protease. Preferably, the serine protease is a dipeptidyl peptidase. In one aspect preferably the dipeptidyl peptidase is DPP-II. In another aspect preferably the dipeptidyl peptidase is DPP-IV.

The present invention also includes a method for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions comprising administering a compound of the present invention as herein described. Preferably, the compound of the present invention as herein described is administered for the treatment or prophylaxis of diabetes, more preferably Type II diabetes.

The present invention also includes the use of a compound of the present invention as herein described in the manufacture of a medicament for the inhibition of a post proline/analine cleaving protease. As mentioned, preferably the post proline/analine cleaving protease is a serine protease. More preferably, the serine protease is a dipeptidyl peptidase. In one aspect preferably the dipeptidyl peptidase is DPP-II. In another aspect preferably the dipeptidyl peptidase is DPP-IV.

The present invention also includes the use of a compound of the present invention as herein described in the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions.

The present invention also includes a compound the present invention as herein described for use as an active therapeutic substance. Additionally, the present invention includes a compound the present invention as herein described for use in the manufacture of a medicament for the inhibition of serine protease. Further, the present invention inlcudes a compound the present invention as herein described for use in the manufacture of a medicament for the treatment or prophylaxis of metabolic disorders, gastrointestinal disorders, viral disorders, inflammatory disorders, diabetes, obesity, hyperlipidemia, dermatological or mucous membrane disorders, psoriasis, intestinal distress, constipation, autoimmune disorders, encephalomyelitis, complement mediated disorders, glomerulonepritis, lipodystrophy, tissue damage, psychosomatic, depressive, and neuropsychiatric disorders, HIV infection, allergies, inflammation, arthritis, transplant rejection, high blood pressure, congestive heart failure, tumors, and stress-induced abortions.

DETAILED DESCRIPTION OF THE PREFERRED EMBODIMENT

The term "alkyl" refers to a straight or branched chain saturated aliphatic hydrocarbon that may be optionally substituted, with multiple degrees of substitution being allowed. Examples of "alkyl" include, but are not limited to methyl, ethyl, n-propyl, isopropyl, n-butyl, t-butyl, n-pentyl, isobutyl, and the like.

As used throughout this specification, the preferred number of carbon atoms will be represented by, for example, the phrase "$C_x$–$C_y$alkyl" which refers to an alkyl group, as herein defined, containing the specified number of carbon atoms. Similar terminology will apply for other preferred ranges as well.

The term "alkylene" refers to a divalent straight or branched chain aliphatic hydrocarbon radical that may be optionally substituted, with multiple degrees of substitution being allowed. An example of "alkylene" includes, without limitation, methylene, namely —$CH_2$—.

The term "alkenyl" refers to a straight or branched chain aliphatic hydrocarbon, containing one or more carbon-to-carbon double bonds that may be optionally substituted, with multiple degrees of substitution being allowed. Examples include, but are not limited to, vinyl and the like.

As used herein the term "alkenylene" refers to a divalent straight or branched chain aliphatic hydrocarbon radical, containing one or more carbon-to-carbon double bonds, which may be optionally substituted, with multiple degrees of substitution being allowed. An example of "alkenylene" includes, without limitation, vinylene, namely, —CH=CH—.

As used herein the term "alkynyl" refers to a straight or branched aliphatic hydrocarbon containing one or more triple bond, which may optionally be substituted, with multuiple degrees of substitution being allowed. Examples of "alkynyl" as used herein include, but are not limited to, ethynyl and the like.

As used herein the term "alkynylene" refers to a divalent straight or branched chain aliphatic hydrocarbon radical, containing at least one carbon-to-carbon triple bond, that may be further substituted, with multiple degrees of substitution being allowed. An example of "alkynylene" includes, without limitation, ethynylene, namely —C≡C—.

The term "aryl" refers to an aromatic ring system, such as an optionally substituted benzene ring system, such as phenyl. The term encompasses fused systems where one or more optionally substituted benzene rings form, for example, anthracene, phenanthrene, or naphthalene ring systems. The term includes ring(s) optionally substituted, with multiple degrees of substitution being allowed, and also includes an optional alkylene linker, such as $C_1$–$C_6$ alkylene, through which the aryl group may be attached. Examples of "aryl" groups include, but are not limited to phenyl, benzyl, 2-naphthyl, 1-naphthyl, biphenyl, as well as substituted derivatives thereof.

The term "heteroaryl" refers to a monocyclic aromatic ring system, or to a fused bicyclic aromatic ring system comprising two or more aromatic rings. These heteroaryl rings contain one or more nitrogen, sulfur, and/or oxygen atoms, where N-oxides, sulfur oxides, and dioxides are permissible heteroatom substitutions and the rings may be optionally substituted, with multiple degrees of substitution being allowed. The term includes ring(s) optionally substituted, with multiple degrees of substitution being allowed, and also includes an optional alkylene linker, such as $C_1$–$C_6$ alkylene, through which the heteroaryl group may be attached. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "cycloalkyl" refers to a mono- or bi-cyclic hydrocarbon ring system, which may be further substituted with multiple degrees of substitution being allowed, and which optionally includes an alkylene linker through which the cycloalkyl may be attached. Exemplary "cycloalkyl" groups include, but are not limited to, cyclopropyl, cyclobutyl, cyclopentyl, cyclohexyl, and cycloheptyl. When substituted, one preferred substituent location for cycloalkyl groups of the present invention is at the "1-position." To illustrate, without limitation, a preferred location for a substituent is represented below with the substituent referred to as "R":

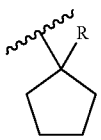

or more generically,

The term "cycloalkyl" includes bridged or fused ring systems, as well, such as hydrindane, decalin, or adamantyl. For ease of reference, also included within the term are cycloalkyl/aryl fused systems where, for example, a cycloalkyl, such as cyclohexyl, is fused with an aromatic ring, such as a benzene ring, to form groups such as

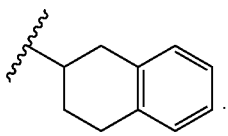

As used herein, the term "heterocyclic" or the term "heterocyclyl" refers to a heterocyclic ring, preferably three to twelve-membered, that is either saturated or has one or more degrees of unsaturation. These heterocyclic rings contain one or more heteroatom, such as nitrogen, sulfur, and/or oxygen atoms, where N-oxides, sulfur oxides, and dioxides are permissible heteroatom substitutions. As used herein heterocyclic groups optionally may be substituted, with multiple degrees of substitution being allowed, and also includes an optional alkylene linker, such as $C_1$–$C_6$ alkylene, through which the heterocyclyl group may be attached. Such a ring may be optionally fused to one or more of another "heterocyclic" ring(s), aryl ring(s), or cycloalkyl ring(s).

Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

The term "halogen" refers to fluorine, chlorine, bromine, or iodine.

As used herein, the term "alkoxy" refers to the group —$OR_a$, where $R_a$ is alkyl as herein defined.

As used herein, the term "amino" refers to the group —$NH_2$.

As used herein, the term "alkylamino" refers to the group —$N(R_a)_2$, where one $R_a$ is alkyl and the other $R_a$ independently is H or alkyl, as herein defined.

As used herein, the term "cycloalkylamino" refers to the group —$N(R_a)_2$, where one $R_a$ is cycloalkyl and the other $R_a$ independently is H or cycloalkyl, as herein defined.

As used herein, the term "arylamino" refers to the group —$N(R_a)_2$, where one $R_a$ is aryl and the other $R_a$ independently is H or aryl, as herein defined.

As used herein, the term "heteroarylamino" refers to the group —$N(R_a)_2$, where one $R_a$ is heteroaryl and the other $R_a$ independently is H or heteroaryl, as herein defined.

Also, as used herein throughout the present specification, the phrase "optionally substituted" denotes an optional substitution, one or more times, with acyl; alkyl; alkenyl; alkynyl; alkylsulfonyl; alkoxy; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; —R'OR'R$^4$; or —NR$^4$R$^5$; where for each occurrence R' is alkylene, alkenylene, or alkynylene, and R$^4$ and R$^5$ are each independently selected from H, alkyl, alkenyl, alkynyl, cycloalkyl, heterocyclyl, aryl, heteroaryl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or R$^4$ and R$^5$ may combine to form a ring, optionally having additional heteroatoms, optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of the present invention may have the ability to crystallize in more than one form, a characteristic known as polymorphism. All polymorphic forms ("polymorphs") are within the scope of the present invention. Polymorphism generally can occur as a response to changes in temperature or pressure, or both, and can also result from variations in the crystallization process. Polymorphs can be distinguished by various physical characteristics that are known in the art such as x-ray diffraction patterns, solubility, and melting point.

Certain of the compounds described herein contain one or more chiral centers, or may otherwise be capable of existing as multiple stereoisomers. The scope of the present invention includes pure stereoisomers as well as mixtures of stereoisomers, such as purified enantiomers/diasteromers or enantiomerically/diastereomerically enriched mixtures. Also included within the scope of the invention are the individual isomers of the compounds per se, as well as any wholly or partially equilibrated mixtures thereof. The present invention covers the individual isomers of the compounds represented by the formulas above as mixtures with isomers thereof in which one or more chiral centers are inverted.

As noted above, the present invention includes salts, solvates, and pharmaceutically functional derivatives of the compounds of the present invention. Salts include addition salts, metal salts, or optionally alkylated ammonium salts. Examples of such salts include hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methane sulphonic, ethane sulphonic, picric, and the like. Further salts include lithium, sodium, potassium, magnesium, and the like. Still further salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, laurate, malate, mandelate, mesylate, methylbromide, methylnitrate, methylsulfate, monopotassium maleate, mucate, napsylate, nitrate, N-methylglucamine, pamoate (embonate), palmitate, pantothenate, phosphate/diphosphate, polygalacturonate, potassium, salicylate, sodium, stearate, subacetate, tannate, tartrate, teoclate, tosylate, triethiodide, trimethylammonium, and valerate salts. Reference is also made to *Journal of Pharmaceutical Science,* 1997, 66, 2, incorporated herein by reference, as relevant to salts.

As used herein, the term "solvate" refers to a complex of variable stoichiometry formed by a solute or a salt or pharmaceutically functional derivative thereof and a solvent. Such solvents for the purpose of the invention should not interfere with the biological activity of the solute. Examples of solvents include, but are not limited to water, methanol, ethanol, and acetic acid. Preferably the solvent used is a pharmaceutically acceptable solvent. Examples of pharmaceutically acceptable solvents include water, ethanol, and acetic acid.

The term "pharmaceutically functional derivative" refers to any pharmaceutically acceptable derivative of a compound of the present invention, for example, an ester or an amide, which upon administration to a mammal is capable of providing (directly or indirectly) a compound of the present invention or an active metabolite or residue thereof. Such derivatives are recognizable to those skilled in the art, without undue experimentation. Nevertheless reference is made to the teaching of *Burger's Medicinal Chemistry and Drug Discovery,* 5$^{th}$ Edition, Vol 1: Principles and Practice, which is incorporated herein by reference to the extent of teaching pharmaceutically functional derivatives.

While compounds of the present invention may be administered as the raw chemical, preferably the compounds of the present invention are presented as an active ingredient within a pharmaceutical formulation as known in the art. Accordingly, the present invention further includes a pharmaceutical formulation comprising a compound of the present invention, or salt, solvate, or pharmaceutically functional derivative thereof together with one or more pharmaceutically acceptable carriers. Optionally, other therapeutic and/or prophylactic ("active") ingredients may be included in the pharmaceutical formulation as well. For example, the compounds of the present invention may be combined with other anti-diabetic agents, such as one or more of the following agents: insulin, α-glucosidase inhibitors, biguanides, insulin secretagogue, or insulin sensitizers. Non-limiting examples of α-glucosidase inhibitors include acarbose, emiglitate, miglitol, and voglibose. Non-limiting examples of biguanides include metformin, buformin, and phenformin. Non-limiting examples of insulin secretagogues include sulphonylureas. Non-limiting examples of insulin sensitizers include peroxisome proliferator activated receptor (PPAR) ligands, such as PPAR-γ agonists, for example Actos™ and Avandia™.

Formulations of the present invention include those especially formulated for oral, buccal, parental, transdermal, inhalation, intranasal, transmucosal, implant, or rectal administration. Among the variety of administrations, oral administration typically is preferred. For oral administration tablets, capsules, and caplets may contain conventional excipients such as binding agents, fillers, lubricants, disintegrants, and/or wetting agents. Non-limiting examples of binding agents include syrup, acacia, gelatin, sorbitol, tragacanth, mucilage of starch, or polyvinylpyrrolidone (PVP). Non-limiting examples of fillers include, for example, lactose, sugar, microcrystalline cellulose, maize-starch, calcium phosphate or sorbitol. Non-limiting examples of lubricants include, for example, magnesium sterate, stearic acid, talc, polyethylene glycol or silica. Non-limiting examples of disintegrants include, for example, potato starch or sodium starch glycollate. A non-limiting example of a wetting agent includes sodium lauryl sulfate. The tablets additionally may be coated according to methods known in the art.

Alternatively, the compounds of the present invention may be incorporated into oral liquid preparations such as aqueous or oily suspensions, solutions, emulsions, syrups, or elixirs. Moreover, formulations containing these compounds may be presented as a dry product for constitution with water or other suitable vehicle before use. Liquid preparations may contain conventional additives. Non-limiting examples of such additives include suspending agents such as sorbitol syrup, methyl cellulose, glucose/sugar syrup, gelatin, hydroxyethylcellulose, carboxymethyl cellulose, aluminum sterate gel or hydrogenated edible fats. Additionally, emulsifying agents such as lecithin, sorbitan monooleate or acacia; non-aqueous vehicles (which may include edible oils) such as almond oil, fractionated coconut oil, oily esters, propylene glycol or ethyl alcohol my be included. Further, preservatives such as methyl or propyl p-hydroxybenzoates or sorbic acid, may be incorporated into the preparation. Such preparations may also be formulated as suppositories, for example, containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, for example, sterile, pyrogen-free water, before use.

The formulations according to the invention may also be formulated as a depot preparation. Such long acting formulations may be administered by implantation, for example, subcutaneously or intramuscularly, or by intramuscular injection. Accordingly, the compounds of the invention may be formulated with suitable polymeric or hydrophobic materials, such as an emulsion in an acceptable oil, ion exchange resins, or as sparingly soluble derivatives, such as a sparingly soluble salt.

Pharmaceutical formulations may be presented in unit dose forms containing a predetermined amount of active ingredient per unit dose. Such a unit may contain certain amounts of a compound of the present invention depending on the condition being treated, the route of administration, and the age, weight and condition of the patient. Examples of such amounts include the formulation containing about 0.1 to about 99.9% active ingredient. Preferred unit dosage formulations are those containing a predetermined dose, such as a daily dose, or an appropriate fraction thereof, of an active ingredient. Such pharmaceutical formulations may be prepared by any of the methods well known in the pharmacy art.

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The therapeutically effective amount of a compound of the present invention will depend upon a number of factors including, for example, the age and weight of the animal, the precise condition requiring treatment and its severity, the nature of the formulation, and the route of administration. Therapeutic effectiveness ultimately will be at the discretion of the attendant physician or veterinarian. An effective amount of a salt or solvate, or pharmaceutically functional derivative thereof, may be determined as a proportion of the effective amount of a compound of the present invention per se. Dosages may vary, depending upon the appropriate inhibition of DPP-IV for purposes of treatment or prophylaxis of a variety of metabolic, gastrointestinal, viral, and inflammatory diseases, including, but not limited to, diabetes, obesity, hyperlipidemia, dermatological or mucous membrane disorders, psoriasis, intestinal distress, constipation, autoimmune disorders such as encephalomyelitis, complement mediated disorders such as glomerulonepritis, lipodystrophy, and tissue damage, HIV infection, allergies, inflammation, arthritis, transplant rejection, high blood pressure, congestive heart failure, tumors, and stress-induced abortions, for example cytokine-mediated murine abortions.

No toxicological effects are indicated/expected when a compound of the present invention is administered in the above mentioned dosage range.

The present invention should be interpreted to cover all combinations of particular and preferred groups herein described. The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims hereto appended.

The following examples illustrate aspects of this invention, but should not be construed as limitations. As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

IUPAC names are included to further identify particular compounds of the present invention. The IUPAC names stated herein should in no way limit the scope of the present invention.

EXPERIMENTALS

In accordance with the present invention and as below, one embodiment of the compounds of the present invention can be prepared by reacting a compound of formula II with an α-amino carboxylate or with an α-amino activated carboxylate, both designated herein generally as aminocarboxylates, under standard coupling conditions, for example, with HATU, DMF, Hunigs base.

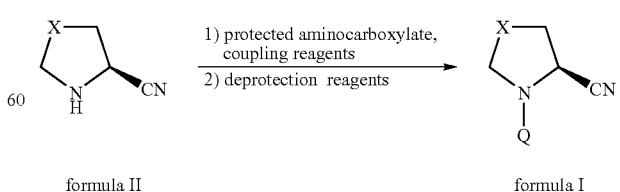

More specifically, a compound of formula II may be reacted with an amino carboxylate, where the amino carboxylate is suitably protected, for example on the α-nitrogen, with an appropriate protecting group such as, for example, a t-butyl carboxy protecting group.

In an alternate embodiment, a compound of formula II may be reacted with an amino activated carboxylate, such as, for example, N-hydroxysuccinimide ester or acid chloride, where the amino activated carboxylate is suitably protected, for example, on the α-nitrogen with an appropriate protecting group such as, for example, a t-butyl carboxy protecting group. Removal of the protecting group under suitable conditions, such as, for example, trifluoroacetic acid for the removal of the t-butyl carboxy, then generates compounds of formula (I).

For further detail regarding the preparation of amino carboxylates for use in preparing the compounds of the present invention, reference may be had to WO 95/15309 and WO 98/19998, each herein incorporated by reference as related to the preparation of such reactants.

EXAMPLES

Example 1

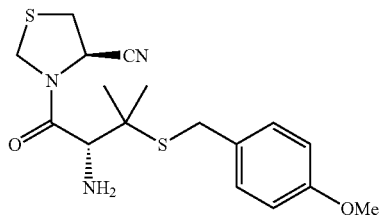

(4R)-3-{(2R)-2-Amino-3-[(4-methoxybenzyl)thio]-3-methylbutanoyl}-1,3-thiazolidine-3-carbonitrile hydrochloride A. tert-Butyl(1R)-1-{[(4R)-4-(aminocarbonyl)-1,3-thiazolidin-3-yl]carbonyl}-2-[(4-methoxybenzyl)thio]-2-methylpropylcarbamate To a stirred solution of N-BOC-L-Pen(MOB)-OH (300 mg, 0.812 mmol) in DMF (8 mL) was added (4R)-1,3-thiazolidine-4-carboxamide hydrochloride (149 mg, 0.812 mmol), HATU (309 mg, 0.812 mmol), and N,N-diisopropylethylamine (0.424 mL, 2.44 mmol). The reaction mixture was stirred at RT for 16 hours. Water (8 mL) was added and the reaction mixture was extracted with five portions of EtOAc. The combined extracts were washed with water, saturated CuSO$_4$, brine, dried over MgSO$_4$, filtered, and concentrated in vacuo. The crude material was flash chromatographed over silica gel (1:1 hexanes:EtOAc) to afford 288 mg (740% yield) of compound A as a colorless oil.

$^1$H NMR (CDCl$_3$) 400 MHz δ 7.18 (d, J=8.6 Hz, 2H), 6.9 (br s, $_1$H), 6.83 (d, J=8.5Hz, 2H), 5.52 (br s, 1H), 5.41 (d, J=9.4 Hz, 1H), 5.10 (dd, J=6.9, 2.8 Hz, 1H), 4.87 (d, J=8.4 Hz, 1H), 4.70 (m, 2H), 3.81 (s, 2H), 3.78 (s, 3H), 3.43 (d, J=14.1 Hz, 1H), 3.15 (dd, J=11.7, 7.0 Hz, 1H), 1.45 (s, 3H), 1.43 (s, 9H), 1.41 (s, 3H) ppm.

B. tert-Butyl (1R)-1-{[(4R)-4-cyano-1,3-thiazolidin-3-yl]carbonyl}-2-[(4-methoxybenzyl)thio]-2-methylpropylcarbamate To a stirred solution of compound A (288 mg, 0.595 mmol) in CH$_2$Cl$_2$ (6 mL) was added trifluoroacetic anhydride (0.168 mL, 1.19 mmol). The reaction mixture was stirred at RT for 5 hours. The reaction mixture was concentrated in vacuo and purified via flash chromatography over silica gel (2:1 hexanes:EtOAc) to give 84 mg (30% yield) of compound B as a colorless oil.

$^1$H NMR (CDCl$_3$) 400 MHz δ 7.28 (d, J=8.6 Hz, 2H), 6.83 (d, J=8.6 Hz, 2H), 5.40 (d, J=8.9 Hz, 1H), 5.29 (dd, J=5.6, 3.7 Hz, 1H), 4.90–4.83 (m, 2H), 4.51 (d, J=9.2 Hz, 1H), 3.80 (s, 2H), 3.78 (s, 3H), 3.33–3.26 (m, 2H), 1.44 (s, 3H), 1.43 (s, 9H), 1.40 (s, 3H) ppm.

C. (4R)-3-{(2R)-2-Amino-3-[(4-methoxybenzyl)thio]-3-methylbutanoyl}-1,3-thiazolidine-4-carbonitrile hydrochloride To a stirred solution of compound B (84 mg, 0.18 mmol) in 1,4-dioxane (1 mL) was added a solution of 4.0 M HCl in 1,4-dioxane (1.0 mL, 4.0 mmol). The reaction mixture was stirred at RT for 12 hours. The solvent was removed in vacuo, and the resulting oil was triturated with Et$_2$O to produce a light yellow solid. The solid was filtered in vacuo, washed with several portions of Et$_2$O, and dried in vacuo to produce 45 mg (62% yield) of the crude product. This material was purified via semi-preparative HPLC (10% acetonitrile in water ramped over 10 minutes to 90% acetonitrile in water) followed by re-salting with 2.0 M HCl in Et$_2$O to produce 5 mg (7% overall yield) of compound C as a light yellow solid.

$^1$H NMR (MeOH-d$_4$) 400 MHz δ 7.35 (d, J=8.6 Hz, 2H), 6.88 (d, J=8.6 Hz, 2H) 5.29 (t, J=5.5 Hz, 1H), 4.74 (d, J=9.2 Hz, 1H), 4.61 (d, J=9.2 Hz, 1H), 4.17 (s, 1H), 3.91 (dd, J=26.7, 12.7 Hz, 2H), 3.77 (s, 3H), 3.51–3.42 (m, 2H), 1.57 (s, 3H), 1.44 (s, 3H) ppm.

Example 2

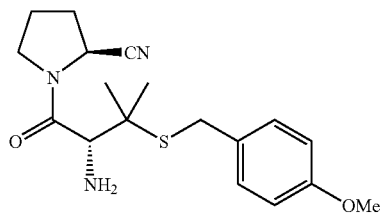

(2S)-1-{(2R)-2-Amino-3-[(4-methoxybenzyl)thio]-3-methylbutanoyl}pyrrolidine-2-carbonitrile hydrochloride A. tert-Butyl (1R)-1-{[(2S)-2-cyanopyrrolidin-1-yl]carbonyl}-2-[(4-methoxybenzyl)thio]-2-methylpropylcarbamate To a stirred solution of N-BOC-L-Pen(MOB)-OH (200 mg, 0.541 mmol) in DMF (6 mL) was added (2S)-pyrrolidine-2-carbonitrile 4-methylbenzenesulfonate (this compound was prepared as previously described in: *Bioorg. Med. Chem. Lett.* 1996, 6, 1163, Ashworth, D. M. et al., incorporated herein by reference in such regard (145 mg, 0.541 mmol), HATU (206 mg, 0.541 mmol), and N,N-diisopropylethylamine (0.380 mL, 2.164 mmol). The reaction mixture was stirred at RT for approximately 60 hours. Water (6 mL) was added and the reaction mixture was extracted with four portions of EtOAc. The combined extracts were washed with water, saturated CUSO$_4$, brine, dried over MgSO$_4$, filtered, and concentrated in vacuo. The crude material was flash chromatographed over silica gel (1:1 hexanes:EtOAc) to afford 213 mg (84% yield) of compound A as a colorless oil.

$^1$H NMR (CDCl$_3$) 400 MHz δ 7.27 (d, J=8.9 Hz, 2H), 6.82 (d, J=8.5 Hz, 2H), 5.44 (d, J=9.3 Hz, 1H), 4.82–4.79 (m, 1H), 4.52 (d, J=9.5 Hz, 1H), 3.91–3.83 (m, 2H), 3.80 (s, 2H), 3.77 (s, 3H), 2.29–2.10 (m, 4H), 1.43 (s, 12H), 1.40 (s, 3H) ppm.

B. (2S)-1-{(2R)-2-Amino-3-[(4-methoxybenzyl)thio]-3-methylbutanoyl}pyrrolidine-2-carbonitrile.

To a stirred solution of compound A (213 mg, 0.452 mmol) in CH$_2$Cl$_2$ (4 mL) was added TFA (1 mL). The reaction was stirred at RT for 4 hours. The solvent was removed in vacuo and the crude oil was re-dissolved in EtOAc and washed with sat. NaHCO$_3$. The aqueous layer was re-extracted with three portions of EtOAc. The combined extracts were dried over MgSO$_4$, decanted, and concentrated in vacuo. Purification via flash chromatography over silica gel (50% MeOH (with 20% NH$_3$) in CH$_2$Cl$_2$) afforded 75 mg (45% yield) of compound B as a white foam.

$^1$H NMR (CDCl$_3$) 400 MHz δ 7.27 (d, J=8.4 Hz, 2H), 6.83 (d, J=8.6 Hz, 2H), 4.77–4.75 (m, 1H), 3.77 (s, 3H), 3.74 (s, 2H), 3.63–3.46 (m, 3H), 2.26–2.07 (m, 4H), 1.91 (br s, 2H), 1.45 (s, 3H), 1.36 (s, 3H) ppm.

C. (2S)-1-{(2R)-2-Amino-3-[(4methoxybenzyl)thio]-3-methylbutanoyl}pyrrolidine-2-carbonitrile hydrochloride Diethyl ether (4 mL) was added to a flask containing compound B (75 mg, 0.215 mmol). Several drops of acetone were added to allow the solution to become homogeneous. A solution of 2.0 M HCl in Et$_2$O (1.0 mL) was added and the reaction mixture was stirred at RT for 5 minutes. A white solid precipitated during this time. The mixture was concentrated in vacuo to dryness and the solid was dried overnight under high vacuum to give 73 mg (88% yield) of compound C as a white solid.

$^1$H NMR (D$_2$O) 400 MHz δ 7.31 (d, J=8.4 Hz, 2H), 6.88 (d, J=8.4 Hz, 2H), 4.69–4.66 (m, 1H), 3.87–3.74 (m, 3H), 3.69 (s, 3H), 3.56–3.50 (m, 1 H), 3.32–3.26 (m, 1H), 2.82–2.12 (m, 2H), 2.09–1.99 (m, 1H), 1.96–1.89 (m, 1H), 1.44 (s, 3H), 1.29 (s, 3H) ppm.

Example 3

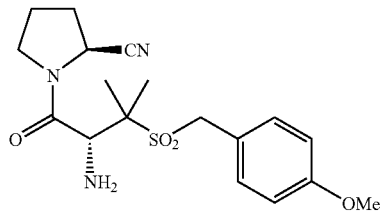

(2S)-1-{(2R)-2-Amino-3-[(4-methoxybenzyl)sulfonyl]-3-methylbutanoyl}pyrrolidine-2carbonitrile hydrochloride

A. tert-Butyl (1R)-1-{[(2S)-2-cyanopyrrolidine-1-yl]carbonyl}-2-[(4-methoxybenzyl)sulfonyl]-2-methylpropylcarbamate To a stirred solution of tert-butyl (1R)-1-{[(2S)-2-cyanopyrrolidin-1-yl]carbonyl}-2-[(4methoxybenzyl)thio]-2-methylpropylcarbamate (427 mg, 0.905 mmol) in chloroform (20 mL) at 0° C. was added solid m-CPBA (1.56 g, 9.05 mmol) in one portion. The reaction mixture was stirred for 30 minutes at 0° C. and then for 14 hours at RT. During this time the reaction mixture went from light purple to colorless to light yellow. The reaction mixture was washed with 1 M NaOH and separated. The aqueous layer was re-extracted with chloroform and the combined extracts were dried over MgSO$_4$, filtered, and concentrated in vacuo. Purification via flash chromatography over silica gel (1:1 hexanes:EtOAc) afforded 355 mg (82% yield) of compound A as a white solid.

$^1$H NMR (CDCl$_3$) 400 MHz δ 7.32 (d, J=8.8 Hz, 2H), 6.88 (d, J=8.6 Hz, 2H), 5.49 (d, J=9.6 Hz, 1H), 5.15 (d, J=9.9 Hz, 1H), 4.76–4.73 (m, 1H), 4.22 (s, 2H), 3.93–3.88 (m, 1H), 3.82–3.78 (m, 1H), 3.78 (s, 3H), 2.29–2.12 (m, 4H), 1.55 (s, 3H), 1.47 (s, 3H), 1.42 (s, 9H) ppm.

B. (2S)-1-{(2R)-2-Amino-3-[(4-methoxybenzyl)sulfonyl]-3-methylbutanoyl}pyrrolidine-2-carbonitrile To a stirred solution of compound A (355 mg, 0.740 mmol) in CH$_2$C$_2$ (6.5 mL) was added TFA (1.5 mL). The reaction mixture was stirred at RT for 2 hours and then concentrated in vacuo. After re-dissolving in EtOAc, the reaction mixture was washed with saturated NaHCO$_3$. The aqueous layer was re-extracted with three portions of EtOAc, and the combined extracts were dried over MgSO$_4$, decanted, and concentrated in vacuo. Purification via flash chromatography over silica gel (5% MeOH (with 2% NH$_3$) in CH$_2$Cl$_2$) afforded 74 mg (27% yield) of compound B as a light yellow oil.

$^1$H NMR (CDCl$_3$) 400 MHz δ 7.33 (d, J=8.8 Hz, 2H), 6.91 (d, J=8.8 Hz, 2H), 4.78–4.75 (m, 1H), 4.62 (d, J=13.4 Hz, 1H), 4.39 (s, 1H), 4.35 (d, J=13.3 Hz, 1H), 3.82–3.77 (m, 1H), 3.80 (s, 3H), 3.68–3.62 (m, 1H), 2.32–2.14 (m, 4H), 1.62 (s, 3H), 1.39 (s, 3H) ppm.

C. (2S)-1-{(2R)-2-Amino-3-[(4-methoxybenzyl)sulfonyl]-3-methylbutanoyl}pyrrolidine-2-carbonitrile hydrochloride Diethyl ether (4 mL) was added to a flask containing compound B (74 mg, 0.198 mmol). Several drops of acetone and CH$_2$Cl$_2$ were added to allow the solution to become homogeneous. A solution of 2.0 M HCl in Et$_2$O (2.0 mL) was added and the reaction mixture was stirred at RT for 5 minutes. A white solid precipitated during this time. The mixture was concentrated in vacuo to dryness and the solid was dried overnight under high vacuum to give 66 mg (80% yield) of compound C as a white solid.

$^1$H NMR (D$_2$O) 400 MHz δ 7.28 (d, J=8.5 Hz, 2H), 6.93 (d, J=8.7 Hz, 2H), 4.75–4.71 (m, 2H), 4.53 (s, 2H), 3.70 (s, 3H), 3.66–3.59 (m, 2H), 2.27–2.17 (m, 2H), 2.09–1.94 (m, 2H), 1.63 (s, 3H), 1.47 (s, 3H) ppm.

Example 4

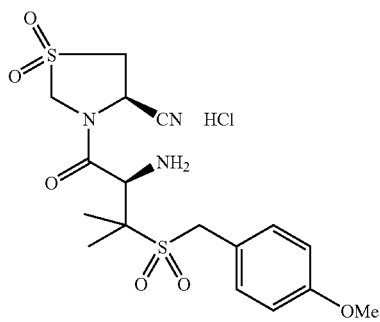

(4R)-3-{(2R)-2-Amino-3-[(4-methoxybenzyl)sulfonyl]-3-methylbutanoyl}-1,3-thiazolidine-4-carbonitrile 1,1-dioxide hydrochloride

A. tert-Butyl (1R)-1-{[(4R)-4-cyano-1,1-dioxido-1,3-thiazolidin-3-yl]carbonyl}-2-[(4-methoxybenzyl)sulfonyl]-2-methylpropylcarbamate To a stirred solution of tert-butyl (1R)-1-{[(4R)-4-cyano-1,3-thiazolidin-3-yl]carbonyl}-2-[(4-methoxybenzyl)thio]-2-methylpropylcarbamate (151 mg, 0.324 mmol) in chloroform (8 mL) was added m-CPBA (560 mg, 3.24 mmol). The reaction mixture was stirred at RT for 14 hours. The reaction mixture was then washed with 1 M NaOH and separated. The aqueous layer was re-extracted with chloroform and the combined extracts were dried over MgSO$_4$, filtered, and concentrated in vacuo. Purification via flash chromatography over silica gel (1:1 hexanes:EtOAc) afforded 121 mg (70% yield) of compound A as a white solid.

$^1$H NMR (CDCl$_3$) 400 MHz δ 7.33 (d, J=8.2 Hz, 2H), 6.92 (d, J=8.6 Hz, 2H), 5.50–5.42 (m, 2H), 5.21–5.12 (m, 1H), 4.88 (d, J=9.2 Hz, 1H), 4.71 (d, J=11.5 Hz, 1H), 4.29–4.20 m, 2H), 3.81 (s, 3H), 3.62–3.45 (m, 2H), 1.54 (s, 3H), 1.52 (s, 3H), 1.43 (s, 9H) ppm.

B. (4R)-3-{(2R)-2-Amino-3-[(4-methoxybenzyl)sulfonyl]-3-methylbutanoyl}-1,3-thiazolidine-4-carbonitrile 1,1-dioxide To a stirred solution of compound A (121 mg, 0.228 mmol) in CH$_2$Cl$_2$ (2.0 mL) was added TFA (0.5 mL). The reaction mixture was stirred at RT for 2 hours and then concentrated in vacuo. After re-dissolving in EtOAc, the reaction mixture was washed with saturated NaHCO$_3$. The aqueous layer was re-extracted with three portions of EtOAc, and the combined extracts were dried over MgSO$_4$, decanted, and concentrated in vacuo. Purification via flash chromatography over silica gel (2% MeOH (with 2% NH$_3$) in CH$_2$Cl$_2$ to 5% MeOH (with 2% NH$_3$) in CH$_2$Cl$_2$) afforded 48 mg (49% yield) compound B as a light yellow oil.

$^1$H NMR (CDCl$_3$) 400 MHz δ (major rotomer) 7.32 (d, J=8.4 Hz, 2H), 6.92 (d, J=8.6 Hz, 2H), 5.52 (dd, J=8.1, 5.2 Hz, 1H), 4.91 (d, J=11.6 Hz, 1H), 4.56 (d, J=9.3 H), 4.53 (d, J=11.1 Hz, 1H), 4.32–4.06 (m, 2H), 3.81 (s, 3H), 3.60–3.51 (m, 2H), 1.99 (br s, 2H), 1.57 (s, 3H), 1.40 (s, 3H) ppm.

C. (4R)-3-{(2R)-2-Amino-3-[(4-methoxybenzyl)sulfonyl]-3-methylbutanoyl}-1,3-thiazolidine-4-carbonitrile 1,1-dioxide hydrochloride Diethyl ether (4 mL) was added to a flask containing compound B (48 mg, 0.112 mmol). Several drops of acetone were added to allow the solution to become homogeneous. A solution of 2.0 M HCl in Et$_2$O (1.0 mL) was added and the reaction mixture was stirred at RT for 5 minutes. A white solid precipitated during this time. The mixture was concentrated in vacuo to dryness and the solid was dried overnight under high vacuum to give 36 mg (86% yield) of compound C as a white solid.

$^1$H NMR (D$_2$O) 400 MHz δ 7.30 (d, J=8.0 Hz, 2H), 6.95 (d, J=8.0 Hz, 2H), 5.62–5.59 (m, 1H), 4.98 (d, J=11.5 Hz, 1H), 4.88 (d, J=11.3 Hz, 1H), 4.70 (s, 1H), 4.59–4.51 (m, 2H), 3.99–3.87 (m, 2H), 3.72 (s, 3H), 1.64 (s, 3H), 1.52 (s, 3H) ppm.

Example 5

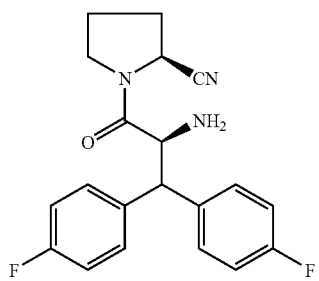

(2S)-1-[(2S)-2-Amino-3,3-bis(4-fluorophenyl)propanoyl]pyrrolidine-2-carbonitrile hydrochloride

A. tert-Butyl (1S)-1-[bis(4-fluorophenyl)methyl]-2-[(2S)-2-cyanopyrrolidin-1-yl]-2-oxoethylcarbamate To a stirred solution of (2S)-2-[(tert-butoxycarbonyl)amino]-3,3-bis(4-fluorophenyl)propanoic acid (475 mg, 1.26 mmol; for the preparation of this compound see below) in DMF (12 mL) was added (2S)-pyrrolidine-2-carbonitrile 4-methylbenzenesulfonate (338 mg, 1.26 mmol), HATU (479 mg, 1.26 mmol), and diisopropylethylamine (0.658 mL, 3.78 mmol). The reaction mixture was stirred at RT for 16 hours then diluted with water (10 mL). The reaction mixture was extracted with 4 portions of EtOAc, and the combined extracts were washed with water, brine, dried over MgSO$_4$, filtered, and concentrated in vacuo. The crude product was flash chromatographed over silica gel (1:1 hexanes:EtOAc) to afford 335 mg (58% yield) of compound A as a white foam.

$^1$H NMR (CDCl$_3$) 400 MHz δ 7.31–7.25 (m, 2H), 7.21–7.16 (m, 2H), 7.05–6.96 (m, 4H), 5.05–4.96 (m, 2H), 4.62 (t, J=5.5 Hz, 1H), 4.40 (d, J=11.0 Hz, 1H), 3.57 (q, J=9.0 Hz, 1H), 2.75–2.70 (m, 1H), 2.10–2.05 (m, 2H), 1.97–1.88 (m, 1H), 1.81–1.70 (m, 1H), 1.33 (s, 9H) ppm.

B. (2S)-1-[(2S)-2-Amino-3,3-bis(4-fluorophenyl) propanoyl]pyrrolidine-2-carbonitrile To a stirred solution of compound A (300 mg, 0.659 mmol) in CH$_2$Cl$_2$ (7 mL) was added TFA (0.507 mL, 6.59 mmol). The reaction mixture was stirred at RT for 12 hours followed by concentration in vacuo. The reaction mixture was re-dissolved in EtOAc and washed with saturated NaHCO$_3$, dried over MgSO$_4$, filtered, and concentrated in vacuo. Purification via flash chromatography over silica gel (30% MeOH (with 2% NH$_3$) in CH$_2$Cl$_2$) afforded 129 mg (55% yield) of compound B as a white solid.

$^1$H NMR (CDCl$_3$) 400 MHz δ 7.33–7.30 (m, 2H), 7.22–7.19 (m, 2H), 7.09 (t, J=8.5 Hz, 2H), 6.98 (t, J=8.6 Hz, 2H), 4.65 (dd, J=7.7, 3.5 Hz, 1H), 4.30 (d, J=10.2Hz, 1H), 4.09 (d, J=10.1 Hz, 1H), 3.37 (q, J=9.0 Hz, 1H), 2.67 (dt, J=8.6, 3.6 Hz, 1H), 2.22–2.00 (m, 4H), 1.96–1.87 (m, 1H), 1.81–1.70 (m, 1H) ppm.

C. (2S)-1-[(2S)-2-Amino-3,3-bis(4-fluorophenyl) propanoyl]pyrrolidine-2-carbonitrile hydrochloride Diethyl ether (6 mL) was added to a flask containing compound B (129 mg, 0.363 mmol). Several drops of acetone were added in order to allow the solution to become homogeneous. A solution of 2.0 M HCl in Et$_2$O (2.0 mL) was added and the reaction mixture was stirred at RT for 5 minutes. A white solid precipitated during this time. The solid was collected via vacuum filtration on a glass frit and dried overnight under high vacuum to give 117 mg (82% yield) of compound C as a white solid.

$^1$H NMR (D$_2$O) 400 MHz δ 7.52–7.45 (m, 2H), 7.31–7.24 (m, 2H), 7.10 (t, J=7.3 Hz, 2H), 6.98 (t, J=7.9 Hz, 2H), 4.83 (d, J=11.3 Hz, 1H), 4.60–4.54 (m, 1H), 4.41 (d, J=11.1 Hz, 1H), 3.44–3.34 (m, 1H), 2.78–2.69 (m, 1H), 2.12–2.01 (m, 1H), 1.97–1.87 (m, 1H), 1.83–1.72 (m, 1H), 1.58–1.46 (m, 1H) ppm.

Preparation of (2S)-2-[(tert-butoxycarbonyl)amino]-3,3-bis(4-fluorophenyl)propanoic Acid (Referenced Above in Example 5)

A. 3,3-Bis(4-fluorophenyl)-3-hydroxypropanoic acid.

To an anhydrous THF (80 mL) solution of n-butyl lithium (46 mL of 2.5 M, 115 mmol) at 0° C. was added dropwise diisopropylamine (11.13 g, 115 mmol) and the solution stirred for 10 minutes. Keeping the solution at 0° C., acetic acid (2.64 g, 44 mmol) was added dropwise and the mixture stirred for 10 min and it was then heated 50° C. After 30 min a heavy precipitate had formed and the solution was allowed to cool. A solution of 4,4'-diflurobenzophenone (9.6 g, 0.044 mol) in THF (50 mL, anhydrous) was added at 0° C., and the solution stirred at room temperature overnight. Water (100 mL) and diethyl ether (100 mL) were added and the aqueous layer was separated and acidified with 1M HCl to pH 3. The organics were extracted with ethyl acetate (3×200 mL) followed by drying over MgSO$_4$. Filtration and removal of the solvent in vacuo yielded a crude white solid that could be washed with cold CHCl$_3$ to remove trace amounts of the benzophenone. The solid was dried under high vacuum yielding 5.63 g (20.2 mmol, 46% yield) of compound A as a white solid.

$^1$H NMR (d$_6$-DMSO) 400 MHz δ 12.4 (s(br), 1H), 7.48–7.39 (m, 4H), 7.19–7.02 (m, 4H), 5.91 (s(br), 1H), 3.25 (s, 2H) ppm.

B. 3,3-Bis(4-fluorophenyl)acrylic acid

To a 20% solution of sulfuric acid in acetic acid (50 mL, V/V) was compound A (5.6 g, 20.2 mmol) and the mixture stirred for 30 minutes at RT. To this solution was added H$_2$O (500 mL) and the organics were extracted with ethyl acetate (3×150 mL) followed by drying over MgSO$_4$. Filtration and removal of the solvent in vacuo yielded a white solid. The solid was dried under high vacuum yielding 4.97 g (19.1 mmol, 95% yield) of compound B as a white solid.

1H NMR (CDCl$_3$) 400 MHz δ 7.27–7.21 (m, 2H), 7.19–7.13 (m, 2H), 7.10–6.95 (m, 4H), 6.26 (s, 1H) ppm C. 3,3-Bis(4-fluorophenyl)propanoic acid To a solution of compound B (2.5 g, 9.61 mmol) in ethyl acetate (250 mL) was added 10% palladium on carbon (50% w/w) and hydrogenated at 1 atmosphere of hydrogen for 12 hours. The heterogeneous solution was filtered through celite and concentrated in vacuo to provide a yellow oil. The oil was dried under high vacuum yielding 2.40 g (9.16 mmol, 95% yield) of compound C as a yellow oil.

$^1$H NMR (d$_6$-DMSO) 400 MHz δ 12.08 (brs, 1H), 7.40–7.30 (m, 4H), 7.15–7.05 (m, 4H), 4.45 (t, 1H, J=8.1 Hz), 3.05(d, 2H, J=8.1 Hz) ppm.

D. (4S,5R)-3-[3,3-Bis(4-fluorophenyl)propanoyl]-4-methyl-5-phenyl-1,3-oxazolidin-2-one To a THF (50 mL, anhydrous) containing compound C (2.0 g, 7.63 mmol) was added N,N-diisopropylethylamine (1.18 g, 9.16 mmol) and then the solution cooled to −78° C. To this solution was added trimethylacetyl chloride (0.97 g, 8.01 mmol) and the solution warmed to 0° C. over 1 hour. The cloudy mixture was filtered and the filtrate added slowly over 10 min to a solution of the lithiated (4S,5R)-(−)-4-methyl-5-phenyl-2-oxazolidine at −78° C., which was prepared by the dropwise addition of n-butyl lithium (3.0 mL of 2.5 M, 7.63 mmol) to a THF (50 mL) solution of (4S,5R)-(−)-4-methyl-5-phenyl-2-oxazolidinone (1.35 g, 7.63 mmol) at −78° C. which had stirred for 10 min to provide the lithiated (4S,5R)-(−)-4-methyl-5-phenyl-2-oxazolidinone. The yellow mixture was warmed to 0° C. and quenched with H$_2$O (50 mL) and extracted with diethyl ether (3×250 mL) followed by drying over MgSO$_4$. Filtration and removal of the solvent in vacuo yielded a solid. Flash chromatography (silica gel, 20% ethyl acetate/hexanes) provided compound D. The white solid was dried under high vacuum yielding 2.31 g (5.49 mmol, 72% yield) as a white solid.

¹H NMR (d₆-DMSO) 400 MHz δ 7.40–7.25 (m, 9H), 7.18–7.02 (m, 4H), 5.76 (d, 1H, J=7.6 Hz), 4.65 (m, 1H), 4.58 (t, 1H, J=7.6 Hz), 3.72 (dd, 1H, J=6.8, 7.0 Hz) 3.57 (dd, 1H, J=16.8, 7.0 Hz), 0.58 (d, 3H, J=6.7 Hz) ppm.

E. (4S,5R)-3-[(2S)-2-Azido-3,3-bis(4-fluorophenyl)propanoyl]-4-methyl-5-[(1E, 3Z)-1-methylhexa-1,3,5-trienyl]-1,3-oxazolidin-2-one To a THF (50 mL, anhydrous) solution containing compound D (2.0 g, 4.75 mmol) at −78° C. was added dropwise potassium bis(trimethylsilyl)amide (10.0 mL of 0.5 M toluene solution, 4.98 mmol). After stirring for 10 min 2,4,6-triisopropylbenzenesulfonyl azide (trisyl azide) (1.84 g, 5.94 mmol) in THF (10 mL, anhydrous) was added in one portion. After 3 minutes acetic acid was added (1.31 g, 21.8 mmol) at −78° C. and then the reaction quickly warmed to 30° C. and stirred for 1 hr at that temperature generating a light yellow solution. To this solution was added H₂O (100 mL) and the organics were extracted with ethyl acetate (500 mL). After washing with sat. NaHCO₃ (100 mL) and drying over MgSO₄ the solvent was removed in vacuo yielding a yellow oil. Column chromatography (ethyl acetate/hexanes 1:9) provided compound E as a white solid. HPLC showed a single diastereoisomer. The white solid was dried under high vacuum yielding 1.71 g (3.70 mmol, 78% yield) as a white solid.

¹H NMR (CDCl₃) 400 MHz δ 7.42–7.35 (m, H), 7.25–7.18 (m, H), 7.10–7.06 (m, 2H), 7.05–6.92 (m, 2H), 5.95 (d, 1H, J=10.8 Hz), 5.05 (d, 1H, J=7.1 Hz), 4.60 (d, 1H, J=10.8 Hz), 4.38 (m, 1H), 0.95 (d, 3H, J=6.8 Hz) ppm.

F. (2S)-2-Azido-3,3-bis(4-fluorophenyl)propanoic acid

To a THF/H₂O (4:1, 50 mL) solution of compound E (1.5 g, 3.25 mmol) at 0° C. was added a solution of lithium hydroxide (0.272 g, 6.49 mmol) in hydrogen peroxide (1.50 mL of 30% soln in H₂O, 48.75 mmol). The mixture was stirred at 0° C. for 1 hr and then quenched with Na₂SO₄ (6.3 g, 50 mL of 1.0 M solution in H₂O). The THF was removed in vacuo and the solution acidified to pH 1 with 6.0 M HCl at 0° C. The organics were extracted with ethyl acetate (2×200 mL) followed by drying over MgSO₄. Filtration and removal of the solvent in vacuo yielded a clear oil. Column chromatography (EtOAc/hexanes/acetic acid 50:50:1) provided compound F as a white solid. The solid was dried under high vacuum yielding 0.78 g (2.60 mmol, 80% yield) as a white solid.

¹H NMR (CDCl₃) 400 MHz δ 9.60(s(br),₁H), 7.25–7.10 (m, 4H), 7.10–6.95 (m, 4H), 4.50 (d, 2H, J=8.6 Hz) ppm.

G. (2S)-2-Amino-3,3-bis(4-fluorophenyl)propanoic acid

To an ethyl acetate (250 mL) solution of compound F (1.5 g, 4.95 mmol) was added 10% palladium on carbon (10% w/w) and hydrogenated at 1 atmosphere of hydrogen for 12 hr. The heterogeneous solution was filtered through celite (1 g) and the filtrate concentrated in vacuo to provide a clear oil. The oil was dried under high vacuum yielding 1.30 g (4.70 mmol, 95% yield) of compound G as a white solid.

¹H NMR (d₆-DMSO) 400 MHz δ 10.2(s(br), 1H), 7.38–7.27(m, 4H), 7.08–6.98 (m, 4H), 4.25 (d, 1H, J=8.3 Hz), 3.95 (d, 1 H, J=8.3 Hz) ppm.

H. (2S)-2-[(tert-Butoxycarbonyl)amino]-3,3-bis(4-fluorophenyl)propanoic acid

To a CH₂Cl₂ (150 mL) solution containing compound G (1.30 g, 4.69 mmol) was added triethylamine (2.37 g, 23.4 mmol) and di-tert-butyl dicarbonate (1.23 g, 5.63 mmol). After stirring for 12 hr H₂O (50 mL) and CH₂Cl₂ (300 mL) were added and the solution acidified to pH 3 with 1.0 M HCl. Separation of the ethyl acetate layer followed by drying over MgSO₄ and removal of the solvent in vacuo yielded a clear oil. The oil was dried under high vacuum yielding 1.68 g (4.4 mmol, 95% yield) of compound H as a white solid.

¹H NMR (d₆-DMSO) 400 MHz δ 12.4 (s(br), 1H), 7.35–7.22 (m, 4H), 7.15–6.95 (m, 4H), 4.78 (t, 1H, J=8.9 Hz), 4.25 (d, 1H, J=8.9 Hz), 3.05 (m, 1H), 1.20 (s, 3H), 1.15 (s, 6H) ppm.

Biological Data

Materials:

H-Ala-Pro-pNA.HCl was purchased from BACHEM Bioscience Inc. (product no. L-1115). A 500 mM stock solution was prepared with dimethylsulfoxide and stored at −20° C. Gly-Pro-AMC was purchased from Enzyme System Products (product no. AMC-39) and stored at −20° C. as a 10 mM stock solution in dimethylsulfoxide. Test compounds were dissolved to 10 mM in dimethylsulfoxide and this was used as a stock solution for DPP-IV titration assays. Athens Research and Technology, Inc prepared the purified human DPP-IV. The material was isolated from human prostasomes using the method of DeMeester et al., *J. Immunol. Methods* 189, 99–105. (1996), incorporated herein by reference in such regard.

DPP-IV Assay:

Two-fold serial dilutions of test compounds in 100% dimethylsulfoxide were performed in 96-well polystyrene flat bottom plates (Costar, #9017). The average enzymatic activity from wells containing dimethylsulfoxide but lacking test compound was used as a control value for calculating percent inhibition. DPP-IV (20 ng/mL) was mixed in microtiter plates with test compounds, substrate and assay buffer to yield 100 μM H-Ala-Pro-pNA.HCl in 25 mM Tris, pH 7.5, 10 mM KCl, 140 mM NaCl. The intact peptide contains a p-nitrophenylanilide which, when hydrolyzed by DPP-IV, releases the absorbant p-nitrophenylaniline. The absorbency was monitored in 20 minutes intervals at a wavelength of 387 nm using a Molecular Devices SpectraMax 250 absorbency plate reader. The enzymatic activity was determined by estimating the best linear fit to the data. Values for enzymatic activity were taken directly from the linear fit determined by the software on the plate reader.

Data Analysis: The enzymatic activity was determined by estimating the best linear fit to the data. Data reduction was performed using the Microsoft Excel RoboSage.

Determination of IC₅₀ Values: The enzymatic activity was plotted against the concentration of test compound, including [I]=0, and the IC₅₀ determined from a fit of equation 2 to the data.

$$RATE = V_{max}/(1+([I]/IC_{50})) \qquad (2)$$

$V_{max}$ was the best fit estimate of the maximal enzymatic activity.

Determination of $K_i$ Values: $K_i$ values were calculated from $IC_{50}$ values using equation 3 assuming a competitive model.

$$K_i = IC_{50} * \left[1 - \frac{S}{(S + K_m)}\right] \quad (3)$$

The apparent pKi values were >5.0 for each of the examples.

DPP-II Assay:

The intermediate plate contained 5.3 μL of test compound in 2-fold serial dilutions across the plate. A volume of 209 μL of buffer (100 mM sodium acetate pH 5.5) containing substrate (H-Lys-Ala-pNA•2HCl; product no. L-2085; BACHEM Bioscience Inc.:) was added to each well of the intermediate plate, then mixed. The reaction was initiated with the transfer of 180 μL of the substrate/test compound solution to the assay plate containing 20 μL of enzyme. Final concentrations in the assay were 100 nM enzyme and 1000 μM substrate in 100 mM NaOAc, pH 5.5, 2.5% DMSO in a final volume of 200 μL. The absorbance was monitored every 20 minutes for 5 hours at 387 nm using a Molecular Devices SpectraMax 250 absorbance plate reader.

Data Analysis: The enzymatic activity was determined by estimating the best linear fit to the data. Data reduction was performed using the Microsoft Excel RoboSage.

Determination of $IC_{50}$ Values: The enzymatic activity was plotted against the concentration of test compound, including [I]=0, and the $IC_{50}$ determined from a fit of equation 2 to the data.

$$\text{RATE} = V_{max}/(1+([I]/IC_{50})) \quad (2)$$

$V_{max}$ was the best fit estimate of the maximal enzymatic activity.

Determination of $K_i$ Values: $K_i$ values were calculated from $IC_{50}$ values using equation 3 assuming a competitive model.

$$K_i = IC_{50} * \left[1 - \frac{S}{(S + K_m)}\right] \quad (3)$$

Certain compounds of the present invention showed activity for DPP-II, for example pKi values of >7.0 were observed, while others demonstrated selectivity for DPP-IV, discussed hereinabove.

In Vivo Studies:

Age and weight matched male CD1 mice were housed individually at 72° F. and 50% relative humidity with a 12 h light/dark cycle. Animals were dosed by oral gavage with 10 ml/kg vehicle (0.5% methylcellulose (HPMC) with 0.1% Tween 80) or 1 mg/kg test compound in vehicle. The animals were anesthetized with isofluorane for blood collection at the specified times (0–6 hours). Plasma DPP-IV activity was measured using the fluorogenic substrate Gly-Pro-AMC (50 μM) according to the manufacturers specification (Enzyme System Products, Livermore Calif.). The substrate was mixed with 50 mM Tris, pH 7.8 and 20% plasma. The samples were incubated for 20 min at 30° C. and fluorescence measured using a cytofluor spectrofluoremeter with the filters set at 360 nm excitation and 460 nm emission.

All research complied with the principles of laboratory animal care (NIH publication No. 85-23, revised 1985) and GlaxoSmithKline policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound selected from:
   (4R)-3-{(2R)-2-Amino-3-[(4-methoxybenzyl)thio]-3-methylbutanoyl}-1,3-thiazolidine-4-carbonitrile hydrochloride;
   (2S)-1-{(2R)-2-Amino-3-[(4-methoxybenzyl)thio]-3-methylbutanoyl}pyrrolidine-2-carbonitrile hydrochloride;
   (2S)-1-{(2R)-2-Amino-3-[(4-methoxybenzyl)sulfonyl]-3-methylbutanoyl}pyrrolidine-2-carbonitrile hydrochloride;
   (4R)-3-{(2R)-2-Amino-3-[(4-methoxybenzyl)sulfonyl]-3-methylbutanoyl}-1,3-thiazolidine-4-carbonitrile 1,1-dioxide hydrochloride; and
   (2S)-1-[(2S)-2-Amino-3,3-bis(4-fluorophenyl)propanoyl]pyrrolidine-2-carbonitrile hydrochloride.

* * * * *

UNITED STATES PATENT AND TRADEMARK OFFICE
CERTIFICATE OF CORRECTION

PATENT NO. : 7,196,201 B2  Page 1 of 1
APPLICATION NO. : 10/481288
DATED : March 27, 2007
INVENTOR(S) : Haffner et al.

It is certified that error appears in the above-identified patent and that said Letters Patent is hereby corrected as shown below:

On the Title Page:

Item (57) ABSTRACT should read as follows:

--The present invention relates to novel compounds, their use for inhibiting serine proteases, such as dipeptidyl peptidases, such as dipeptidyl peptidase IV (DPP-IV) and to methods for their production and their therapeutic utility.--

Signed and Sealed this

Tenth Day of July, 2007

JON W. DUDAS
*Director of the United States Patent and Trademark Office*